US00PP23544P2

(12) United States Plant Patent
Uebelhart

(10) Patent No.: US PP23,544 P2
(45) Date of Patent: Apr. 16, 2013

(54) ***GAILLARDIA* PLANT NAMED 'LUCKY WHEELER'**

(50) Latin Name: *Gaillardia aristata*
Varietal Denomination: Lucky Wheeler

(75) Inventor: Georg G. Uebelhart, Schwarmstedt (DE)

(73) Assignee: Jelitto Staudensamen GmbH, Schwarmstedt (DE)

( * ) Notice: Subject to any disclaimer, the term of this patent is extended or adjusted under 35 U.S.C. 154(b) by 422 days.

(21) Appl. No.: 12/924,866

(22) Filed: Oct. 7, 2010

(51) Int. Cl.
*A01H 5/00* (2006.01)

(52) U.S. Cl. ..... Plt./431

(58) Field of Classification Search ..... Plt./431
See application file for complete search history.

*Primary Examiner* — Annette Para

(74) *Attorney, Agent, or Firm* — Penny J. Aguirre

(57) ABSTRACT

A new cultivar of *Gaillardia*, 'Lucky Wheeler', characterized by its dwarf habit, large blooms with red centers, yellow tips and fluted petals, its long blooming period, and its good garden performance and winter hardiness.

2 Drawing Sheets

Botanical classification: *Gaillardia aristata.*
Variety denomination: 'Lucky Wheeler'.

CROSS REFERENCE TO A RELATED APPLICATION

This application is co-pending with a U.S. Plant Patent Applications filed for plants derived from the Inventor's breeding program that are entitled *Gaillardia* Plant Named 'Fancy Wheeler' (U.S. Plant Pat. No. 22,016) and *Gaillardia* Plant Named 'Jazzy Wheeler' (U.S. Plant Pat. No. 22,217).

BACKGROUND OF THE INVENTION

The present invention relates to a new and distinct cultivar of *Gaillardia* plant, botanically known as *Gaillardia aristata* 'Lucky Wheeler' and will be referred to hereinafter by its cultivar name, 'Lucky Wheeler'.

'Lucky Wheeler' was derived from a controlled breeding program conducted by the Inventor at his nursery in Schwamstedt, Germany. The breeding program focuses on obtaining new cultivars of *Gaillardia* with compact and floriferous plant habit in a range of flower colors. In summer 2006, the Inventor collected and pooled seeds from open pollination of unnamed plants from his breeding program with accession Nos. G04010, G04045, and G04065. 'Lucky Wheeler' was selected in 2008 by the Inventor as a single unique plant from the resulting seedlings.

Asexual reproduction of the new cultivar was first accomplished via stem cuttings in Lisse, The Netherlands in 2008. The characteristics of this cultivar have been determined to be stable and are reproduced true to type in successive generations.

SUMMARY OF THE INVENTION

The following traits have been repeatedly observed and are determined to be the characteristics of the new cultivar of *Gaillardia*. These attributes in combination distinguish 'Lucky Wheeler' as unique from all other varieties of *Gaillardia* known to the Inventor.

1. 'Lucky Wheeler' exhibits medium sized inflorescences with ray florets having red centers, yellow tips and fluted petals.
2. 'Lucky Wheeler' is hardy in U.S.D.A. Zones 3 to 9.
3. 'Lucky Wheeler' is reliably perennial with a dwarf, spreading habit.
4. 'Lucky Wheeler' produces numerous blooms throughout the growing season.

'Lucky Wheeler' can be compared to its parent plants, which differ in lacking fluted petals and bi-color red and yellow inflorescences and in having taller plant habits. 'Lucky Wheeler' can also be compared to *Gaillardia* cultivars 'Fanfare' (U.S. Plant Pat. No. 15,892) and 'Tizzy' (U.S. Plant Pat. No. 19,944). 'Fanfare' differs from 'Lucky Wheeler' in having a taller and less reliably perennial plant habit, larger flowers, a shorter blooming period, and fewer branches. 'Tizzy' differs from 'Lucky Wheeler' in having a taller and less reliably perennial plant habit, shorter blooming periods, and in having ray florets that lack bi-colored petals. 'Lucky Wheeler' can also be compared to cultivars from the same breeding program 'Fancy Wheeler' and 'Jazzy Wheeler', which both differ from 'Lucky Wheeler' in having larger flowers and in lacking fluted petals.

BRIEF DESCRIPTION OF THE DRAWINGS

The accompanying colored photographs illustrate the overall appearance and distinct characteristics of the new *Gaillardia*. The photographs were taken of a plant two years in age as grown outdoors in a 4-liter container in Lisse, the Netherlands. The photograph in FIG. 1 provides a side view of a 'Lucky Wheeler' in bloom, the photograph in FIG. 2 provides a close-up view of the inflorescences of 'Lucky Wheeler' and the photograph in FIG. 3 provides a close-up view of the inflorescences of 'Lucky Wheeler'. The colors in the photographs are as close as possible with the digital photography and printing techniques utilized and the color codes in the detailed botanical description more accurately describe the colors of the new *Gaillardia.*

DETAILED BOTANICAL DESCRIPTION

Figure 1:
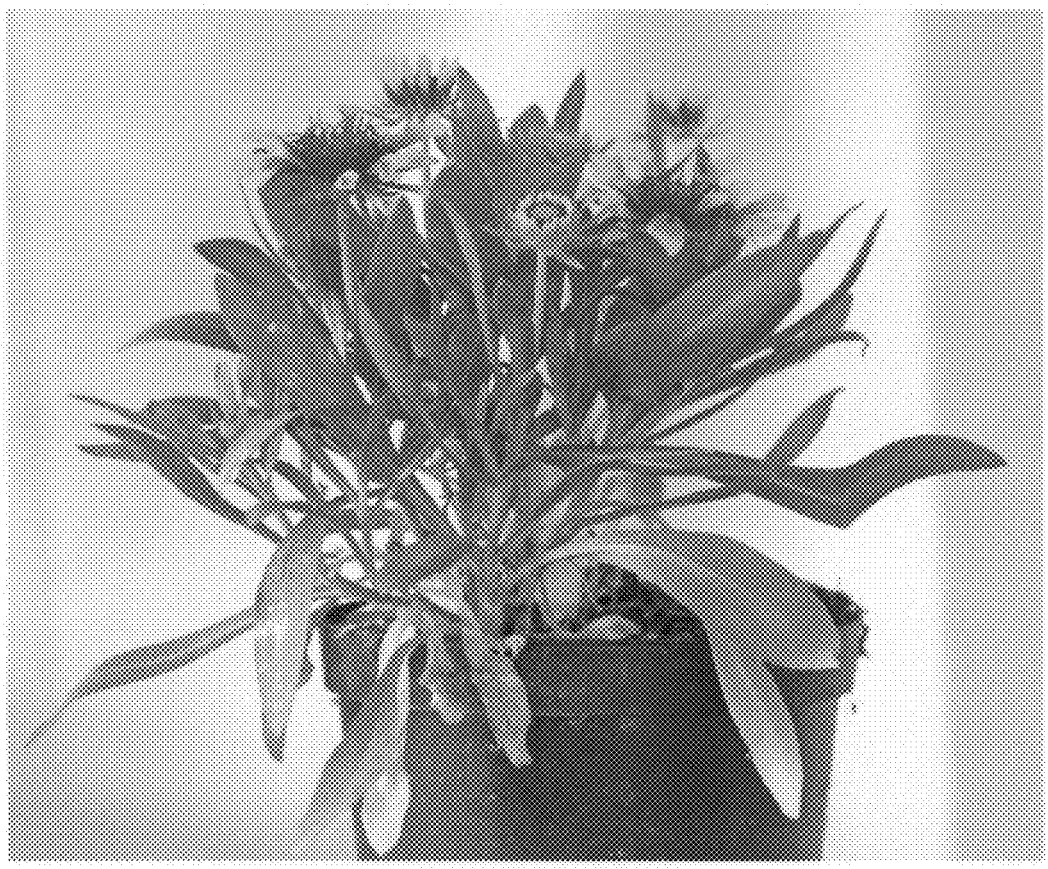
Figure 2:
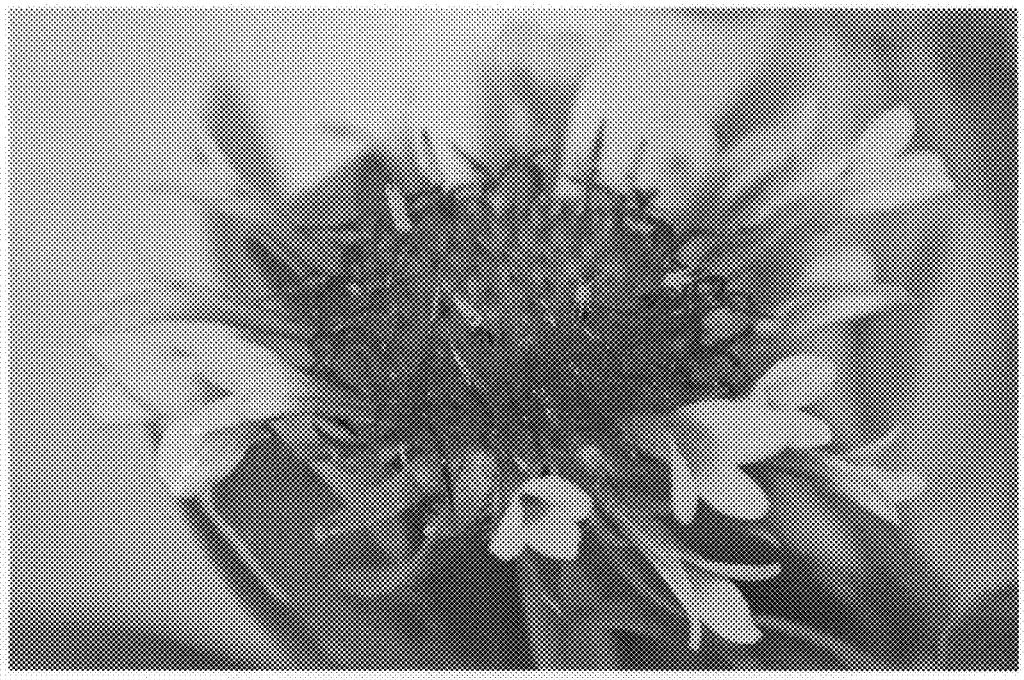
Figure 3:
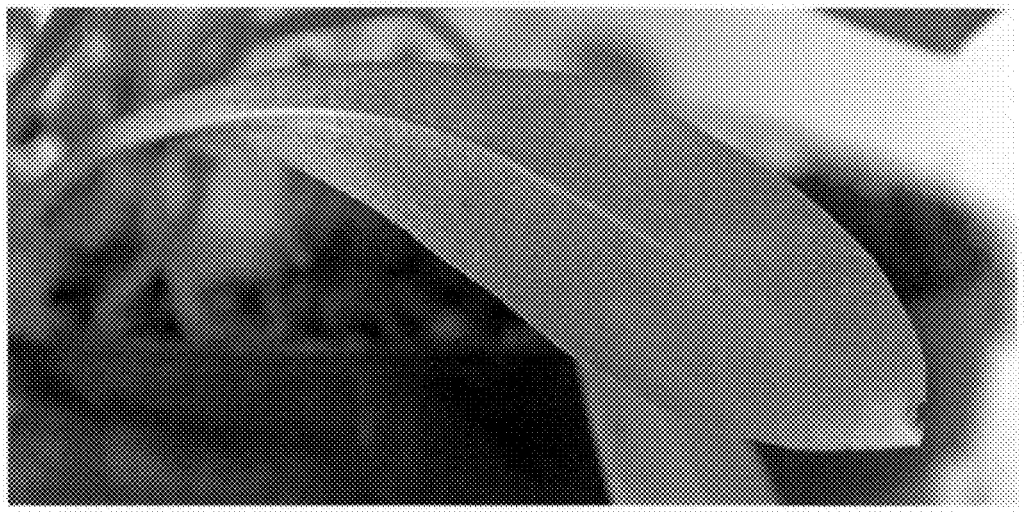

The detailed botanical data was collected in September from plants 13 weeks in age as grown in 1.5-liter containers in cold-storey greenhouse in Noordwijkerhout, The Netherlands with day temperatures ranging between 12° to 26° C. and night temperatures ranging between 4° and 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming season*.—Continuously from mid spring to early October in The Netherlands.

*Plant habit*.—Herbaceous perennial, dwarf, globular in overall shape, broad and upright and spreading growth habit.

*Height and spread*.—About 25 cm in height and 40 cm in width in 2 years, 13 week old plants reach 16.5 cm in height and 23 cm in width.

*Hardiness*.—U.S.D.A. Zones 3 to 9.

*Diseases resistance*.—No susceptibility or resistance to diseases has been observed.

*Root description*.—Fibrous.

Growth and propagation:

*Propagation*.—Stem cuttings and Tissue Culture.

*Time from cutting to flowering*.—Average of 13 weeks.

*Crop maintenance*.—No pinching or pruning required.

*Growth rate*.—Low to moderate, 5 cm per month.

Stem description:

*Stem shape*.—Rounded.

*Stem aspect*.—Average 60° from horizontal.

*Stem strength*.—Moderate.

*Stem color*.—143C.

*Stem surface*.—Densely covered with strigose hairs averaging 1 mm in length and NN155D in color, rough to touch.

*Lateral branch length*.—Average of 8.5 cm (excluding peduncles).

*Lateral branch diameter*.—Average of 3 mm.

*Quantity of lateral branches*.—About 4 per plant in a 1.5-liter container.

*Internode length*.—Average of 1.2 cm.

*Branching*.—Freely branched.

Foliage description:

*Leaf division*.—Simple.

*Leaf shape*.—Broadly oblanceolate to linear-oblong.

*Leaf base*.—Decurrent.

*Leaf apex*.—Broadly acute.

*Leaf margin*.—Entire.

*Leaf venation*.—Pinnate, 144C in color on upper and lower surface.

*Leaf attachment*.—Sessile.

*Leaf arrangement*.—Alternate.

*Leaf surface*.—Upper and lower surfaces; dull, rough to touch, and moderately covered with strigose hairs about 0.5 mm in length and NN155D in color.

*Leaf color*.—Young foliage; upper surface 138A, lower surface 138A to 138B, mature foliage; upper surface and lower surface 138A.

*Leaf size*.—Average of 10.3 cm in length and 1.7 cm in width.

Flower description:

General description:

*Inflorescence type*.—Terminal capitulum with many disc florets, one row of ray florets, and three rows of involucral bracts.

*Rate of flowering*.—Terminal inflorescence opens before lateral inflorescence.

*O of days required for flowering response*.—An average of 9 weeks.

*Lastingness of inflorescence*.—About 2 weeks, persistent.

*Inflorescence aspect*.—Held upright.

*Fragrance*.—Moderately in strength, slightly sweet, chrysanthemum-like.

*Quantity of inflorescences*.—About 12 per plant in a 1.5-liter container.

*Inflorescence buds*.—About 7 mm in depth and 1.3 mm in diameter, flattened globular, color 150C to 150D with center 152B.

*Inflorescence size*.—About 3.1 cm in depth and 5 cm in diameter, diameter of disk about 2.2 cm.

*Receptacle*.—Flattened globular in shape, about 3 mm in depth, 4 mm in diameter, 155D in color.

*Peduncle*.—Round in shape, upright, moderately strong, 138C in color with apex 138D, about 4.8 cm in length and 2 mm in diameter, slightly pubescent with soft hairs 0.5 mm in length and NN155D in color.

*Involucral bracts* (*phyllaries*).—Average of 38 per inflorescence, arranged in 3 rows, lanceolate to narrowly ovate in shape, narrowly acute apex, broadly cuneate base, margin entire and covered in villous hairs 1.5 mm in length NN155D in color, upper surface dull and smooth and lower surface dull and densely covered with short hairs; about 0.5 mm in length and 157D in color, 138B in color becoming 138D towards base, about 1.1 cm in length and 2 mm in width.

Ray florets (capitulate):

*Number*.—Average of 17 (range from 13 to 20).

*Arrangement*.—Rotate, 1 whorl.

*Appearance*.—Upper surface smooth and dull, lower surface dull moderately covered with short hairs 0.8 mm in length and 186C in color.

*Shape*.—Obovate, three-lobed, lower half fused into tube.

*Aspect*.—Outward to slightly upward at an angle of 25° from horizontal.

*Size*.—Average of 2.5 cm in length and 9 mm in width.

*Petal apex*.—Three-lobed.

*Petal base*.—Tubular.

*Petal margins*.—Entire.

*Petal texture*.—Upper surface smooth, lower surface moderately covered with short hairs about 0.8 mm in length and 186C in color.

*Petal color*.—Opening; Upper surface 179A with apex 13A, lower surface 174B to 174C with apex 12A to 13A, fully open; upper surface N34A with apex 13A to 14B, lower surface 178C to 178D with apex 13B, senescing; upper surface 173B with apex 13A, lower surface 179B to 179C with apex 13A.

Disk florets (perfect):

*Quantity*.—Average of 60.

*Shape*.—Tubular with upper 30% free.

*Arrangement*.—Spiral concentric towards center of disc.

*Size*.—About 9 mm in length and 3 mm in width.

*Petal apex*.—Free, narrowly acute, entire margin.

*Petal base*.—Fused.

*Petal texture*.—Upper surface; smooth, slightly glossy, lower surface; strongly hirsute with hairs about 0.7 mm in length, slightly glossy.

*Color*.—When opening upper and lower surface; tip 46A, mid-section 24B and 24C and base 145D, mature upper and lower surface; tip 46A, mid-section 22D and base 145D.

Reproductive organs:

*Presence*.—Disk flowers are perfect, ray flowers are carpellate.

*Gynoecium*.—1 pistil per disk and ray floret, 1.1 cm in length, stigma decurrent and 53A to 53B in color, style 7 mm in length and 150D in color, ovary 145D in color.

*Androecium*.—5 stamen per disk floret, filament 3 mm in length and 157D in color, anther linear in shape, about 4 mm in length and 13B to 13C in color with apex 203A, pollen moderate in quantity and 14A in color.

*Fruit and seed*.—No fruits or seeds observed to date.

It is claimed:

1. A new and distinct variety of *Gaillardia* plant designated 'Lucky Wheeler' as described and illustrated herein.

* * * * *